United States Patent [19]

Piancatelli et al.

[11] 4,413,145
[45] Nov. 1, 1983

[54] PROCESS FOR THE SYNTHESIS OF 3-KETO-CYCLOPENTENE-5-OXY DERIVATIVES HAVING INSECTICIDE ACTIVITY

[75] Inventors: Giovanni Piancatelli; Arrigo Scettri; D'Auria Maurizio, all of Rome, Italy

[73] Assignee: Consiglio Nazionale Delle Ricerche, Rome, Italy

[21] Appl. No.: 287,667

[22] Filed: Jul. 28, 1981

[30] Foreign Application Priority Data

Feb. 11, 1981 [IT]  Italy ................................ 47769 A/81

[51] Int. Cl.³ ...................... C07C 45/45; C07G 13/00
[52] U.S. Cl. .................................. 568/345; 568/353; 568/379; 204/158 R
[58] Field of Search ............... 568/310, 341, 343, 347, 568/353, 379, 345; 560/52, 64; 204/158 R

[56] References Cited

U.S. PATENT DOCUMENTS 3,655,693  4/1972  Shen et al. ........................... 560/52
4,181,807  1/1980  Green .................................. 560/52

OTHER PUBLICATIONS

*Chemical Abstracts*, vol. 89 #59452q "Chem. Phys. Letter" 1978, pp. 543–546.
Buchi et al. *Journal of the American Chemical Society* "A New Synthesis of Rethrolone" Aug. 1971, pp. 4319–4320.
Cooper et al. *Tetrahedron* "The Chemistry of γ Oxosulfones" 1976, pp. 4675–4678.
Floyd *J. Org. Chem.* "Prostaglandins and Congeners" 1978, pp. 1641–1643.
Hirsch et al. "The Hydrolysis of αα'-Dimethoxydihydrofurans" Jun. 1972—pp. 523–529.
Piancatelli et al. *Tetrahedron* "A New Synthesis of Cxocyclopentenes" 1978, pp. 2775–2778.
Romanet et al. *Journal of the American Chemical Society*
"A New and Highly Efficient Synthesis of Rethrolones" Mar. 1974, pp. 3701–3702.
Shono et al. *Chemistry Letters* "A Facile and General Synthesis of 4-Hydroxycyclopentenones" 1976, pp. 1249–1252.
Sih et al. *Journal of American Chemical Society* "Total Synthesis of Prostaglandins" 1973, pp. 1676–1677.
Stork et al. *Journal of the American Chemical Society* "A Route to Prostaglandins . . . " 1975, pp. 3258–3260.
Levisalles "Pyridazines II.-La preparation den pyridazines a partir de derives da furanne", Bull. Chem. Soc. France, 997–1003, (1957).

*Primary Examiner*—Delbert E. Gantz
*Assistant Examiner*—Raymond Covington
*Attorney, Agent, or Firm*—Pollock, Vande Sande & Priddy

[57] ABSTRACT

Process for the synthesis of the 3-keto-cyclopentene-5-oxy derivatives (rethrolones) having the general formula:

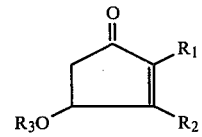

wherein:
R₁ is hydrogen, saturated or unsaturated $C_1$–$C_{10}$ alkyl.
R₂ is saturated or unsaturated $C_1$–$C_{10}$ alkyl.
R₃ is hydrogen or benzoyl characterized as having insecticide activity.

The process comprises as a basic operation the photoisomerization of a transenedicarbonylic intermediate to the corresponding cis form and then its cyclization to a rethrolone.

20 Claims, No Drawings

PROCESS FOR THE SYNTHESIS OF 3-KETO-CYCLOPENTENE-5-OXY DERIVATIVES HAVING INSECTICIDE ACTIVITY

The present invention refers to a process for the synthesis of 3-keto-cyclopentene-5-oxy derivatives having insecticide activity.

Particularly the invention refers to a process to obtain the synthesis of the 3-keto-cyclopentene-5-oxy derivatives group having the general formula:

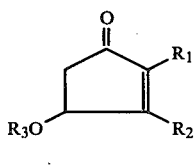

Wherein:

$R_1$ is hydrogen, saturated or unsaturated $C_1$-$C_{10}$ alkyl.

$R_2$ is saturated or unsaturated $C_1$-$C_{10}$ alkyl.

$R_3$ is hydrogen or benzoyl.

characterized by a considerable insecticide activity wherein as fundamental operations the photoisomerization of a transenedicarbonylic intermediate, to the corresponding cis form, and the subsequent cyclization to rethrolone are provided.

As it is known the compounds of formula I are called rethrolones in literature. They are the alcoholic component of the pyrethrins, a group of esters either natural or synthetic, of the chrysanthemic or pyrethric acids, having noticeable insecticide characteristics. Differently from other synthetic insecticides, of the halogenated hydrocarbons, phosphates and carbamate type, to be found more easily and generally more stable, as it is well known, the pyrethrins have the considerable advantage to be biodegradable and much less volatile; besides, they show a low toxicity for mammals. The prior art discloses a great number of methods about the synthesis of the rethrolone, nevertheless generally it is necessary to use very expensive starting products or reactants. Among the more efficient processes it is to be cited those recently disclosed by C. H. Sih, J. B. Heather, G. P. Perruzzotti, P. Price, R. Sood, L. F. H. Lee, *J. Am. Chem. Soc.,* 95, 1676 (1973); G. Stork, G. Garcia, C. Kowalski, *J. Am. Chem. Soc.* 97, 3258 (1975); G. K. Cooper, L. J. Dolby, *Tetr. Letters,* 4675 (1976).

In 1978 a general method to prepare the rethrolones was published by an Italian search group, method which, on the contrary, uses a simple synthetic method, low cost starting products and simple experimental conditions (G. Piancatelli, A. Scettri, M. D'Auria, G. David, *Tetrahedron,* 34, 2775 (1978).

As it is known allethrone is the alcoholic component of allethrin, (a synthetic homologue of natural pyrethrins) commercially more interesting. Furthermore nowadays it is industrially prepared by means of the Schecter method, starting from the allyl chloride, methyl acetate and methylgliossale. This process, dated back to 1949, is characterized by low overall yields. For this reason the requirement to carry out new and more effective synthesis processes has arisen.

Furthermore as regards the allethrone, some processes are known from the prior art which are characterized by expensive and strict operative conditions or by long synthesis operations. Among the most effective methods (at least for the overall yields) it is possible to mention those developed by G. Buchi, D. Minster, J. F. C. Young, *J. Am. Chem. Soc.,* 93, 4319 (1971); M. Vandewalle, E. Madeleyn, *Tetrahedron,* 26, 3551 (1970); R. F. Romanet, R. H. Schlessinger, *J. Am. Chem. Soc.,* 96, 3701 (1974).

Consequently it is the object of this invention to provide a synthesis process for rethrolones which improves the productive yields of the known processes and which reduces the costs, both because of the absence of secondary products or byproducts, and of the simplicity of technology.

It is to be noted that the process according to the invention not only eliminates or reduces in a noticeable measure the aforesaid inconveniences of "prior art", but also presents intrinsic advantages such as, particularly, the utilization as raw material of cyclopentenonic compounds, now considered as byproducts of no interest, as well as the formation from these to intermediates not cited in literature up to now.

Another advantage is the production, according to the fixed operative characteristics, of mixtures of rethrolones of formula (I), that is of compounds with similar structure, the possible pharmacological properties of which can be hypothesized, and therefore are the object of study for researches of industrial interest.

The main technological characteristics of the process according to this invention, may be consequently summarized in the following notes:

(a) Preparation of the raw material for the synthesis of rethrolones by the photoisomerization of transenedicarbonylic compounds with the general formula:

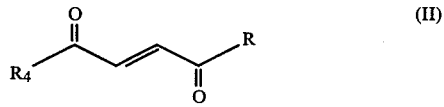

Wherein R is a $C_4$-$C_{10}$ alkyl group and $R_4 = R_2$ of formula I to the corresponding cis-enedicarbonilic compounds with formula:

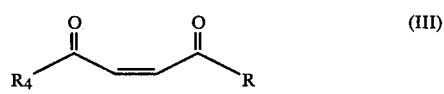

Wherein R has the same meaning of (II).

It has to be noted that the formula (II) compounds have been never used in the rethrolones synthesis but they have been even laid aside as useless byproducts and the formula (III) intermediates, of scarce or no importance in literature, are obtained with good yields and consequently constitute the new products of this invention to be cyclized then to rethrolones (b) The cyclization conditions are critical and have been determined exactly by the examination of influence of bases, temperature and solvent on the transformation reaction of the cis compounds of formula (III), to the formula (I) retholones, a specific object of this invention.

It is useful in any case to consider that the starting substance of this invention is a 2-alkyl-furan, such as 2-methyl-furan, which is transformed, according to standing methods, to the 2.5-dialkyl-furan with the general formula:

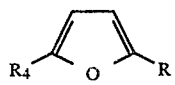

Wherein R and R₄ have the meanings as before said, as for example 2-methyl-5-alkylfuran, by reaction with lithium butyl in tetrahydrofuran at −25° C. and following reaction of the so obtained 5-methyl-2-lithium-furyl with an alkyl bromide R-Br wherein R is a $C_4$–$C_{10}$ alkyl, as for example n-decyl, n-nonyl, 3-butenyl, according to the methodology described by G. Buchi and H. Wuest, *J. Org. Chem.*, 31, 977 (1966).

The so obtained 2,5-dialkyl-furan (IV) is transformed to the trans-enedicarbonylic derivatives (II) by an oxidative breakage reaction of the furan nucleus obtained by chlorochromate pyridinium (PCC) in anhydrous methylene chloride at 50° C. with yields of about 90% or higher, always according to known techniques.

The furanic nucleus has been often utilized as a source of 1.4-dicarbonylic unsaturated alpha, beta components. In 1957 Levisalles (*Bull. Chem. Soc. France*, 997, 1957) described a preparation method for cis-enedicarbonylic compounds starting from 2.5-dimethoxy-2.5-dihydroderivative of a 2.5-dialkylfuran by hydrolysis. The cis-enedicarbonylic derivatives may be isomerized from the trans form by treatment in acid environment. More recently (T. Shono, Y. Matsumura, H. Hamaguchi, K. Nakamura, *Chem. Lett.*, 1249, 1976) the 2.5-dimethoxy-2.5 dihydroderivatives of 2.5-dialkylfurans have been hydrolyzed to cis-enedicarbonylic derivatives by treatment with acid exchange resin.

These operative processes have the limit that the possible functional groups which are present in one or in both alkylic groups may be attacked during the 2.5-dimethoxy-2.5 dihydroderivative preparation with further necessary reactions to restore the original functional groups.

The direct oxidation of 2.5-dialkyl-furans with PCC does not present limitations as those before cited. Surprisingly it has been also found that the so obtained trans-enedicarbonylic compounds may be isomerized to the corresponding cis-derivatives (III) by photochemical isomerization. The formula (II) compounds give by irradiation for a sufficient time, with a mercury vapour lamp of ILESA medium pressure 125 Watt power, a mixture of cis and trans components which, by silica gel chromatography, by benzene ethyl ether 95:5 elution yields the corresponding cis-enedicarbonylic compounds (III), with yields of 80–90%, and the untransformed starting products of formula (II) with yields of 10–20%.

The photoisomerization object of this invention may be obtained with high yields in many solvents such as benzene, dioxane, acetone and methanol.

The photoisomerization does not result sensible to the photosensitizers utilization either with high (acetophenone) or low (benzyl) energy of triplet status. The photoisomerization reaction moreover, does not appear to occur beyond the cis derivative quantities previously said, if the reaction is prolonged in the time when the solvent is acetone, while there is decomposition of the reactant in methanol after 16 hours of irradiation.

The procedure described for formula (III) compounds synthesis is the most used among those described up to date and produces 2.5-dialkylfuran derivatives with practically quantitative yields.

The gamma-dicarbonylic alpha, beta unsaturated compounds of formula III have been often utilized as synthetic intermediates. For instance their utilization in the pyridazines is known (J. A. Hirah, A. J. Szur, J. Heterocyclic Chem., 523, 1972). The formula III compounds have been utilized also as intermediates in the cyclopentenones synthesis. In this case the necessary alcoholic cyclization has been obtained by numerous methodologies; among these of importance are the one proposed by T. Shono, Y. Matsumura, H. Hamaguchi, K. Nakamura, *Chem. Lett.* 1249, 1976, who use sodium carbonate at 100° C., and the one proposed by M. B. Floyd, *J. Org. Chem.*, 43, 1641 (1978), who uses a buffer solution at pH about 5.5 which is constituted of monosodic phosphate and bisodic phosphate.

According to the invention it has been found that the necessary cyclization to obtain formula I compounds may be obtained using a large spectrum of bases either inorganic (e.g. soda) or organic (e.g. aliphatic and aromatic amines) and that it is possible to obtain selectively good yields of one of the two possible products of cyclization by modifying the experimental conditions.

For example, in a first experiment, the cis-enedicarbonylic III compounds solved in dioxane, have been treated with 0.1 N NaOH at 20° C. for 2 hours.

In this case, as an example, by starting from said cis-enedicarbonylic compounds with formula:

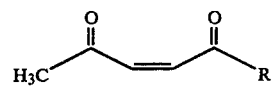

wherein R is a $C_4$–$C_{10}$ alkyl, a 3-keto-cyclopentene-5-oxy mixture is obtained, with general formula (I), constituted of the components:

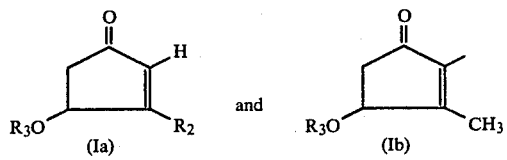

Particularly if in (III) R=n-decyl, it is obtained the mixture with:

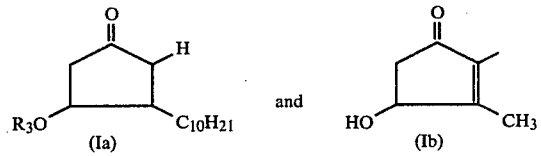

This mixture treated with benzoyl chloride in pyridine at 20° C. for 4 hours yields a raw product which is chromatographed over silica gel by elution with 2:1 n hexane/ethylic ether to yield the two 3-keto-cyclopentenes:

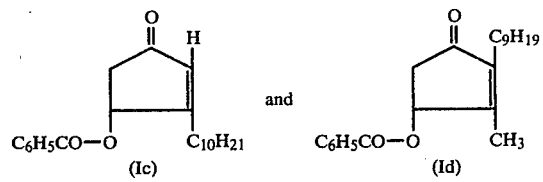

The yield of Ic is 43%, the one of Id is 18%.

If in the cis-enedicarbonylic compound (III) R=3-butenyl, the reaction with NaOH in dioxane at 20° C. yields a mixture which in its turn is reacted with benzoyl chloride in pyridine.

By chromatographic separation the two -ketocyclopentenes

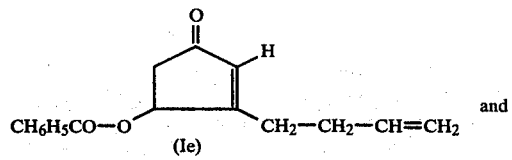
(Ie)

and

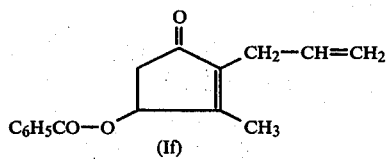
(If)

are obtained.

Yield: Ie: 24%   If: 41%

If the treatment of the formula (III) compounds with 0.1 N NaOH in dioxane is carried out at 100° C., in the case wherein R=n-decyl, a Ic and Id mixture is obtained with yield 20% and 40%, respectively.

If in (III) R=n-butenyl, the treatment with 0.1 N sodium carbonate at 100° C. gives a product only which is chromatographed over silica gel by elution with ethylacetate and precisely:

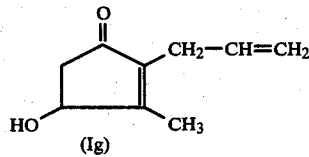
(Ig)

known as (±) allethrone, yield 50%.

From the above it is possible to note that the reaction conditions and particularly the treatment temperature with 0.1 N NaOH in dioxane give mixtures of the two possible reaction products with good selectivity or (Ig) exclusive formation of the desired product without trace of the other one.

Indeed in the case of the two compounds mixtures such as Ia and Ib the desired product is selected by chromatography after transforming the reaction products in the corresponding benzoyl derivatives.

Therefore it is the specific object of this invention to provide a process for the 3-keto-cyclopentene-5-oxy derivatives synthesis (rethrolones) of general formula:

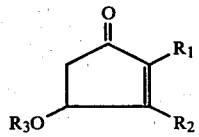
(I)

wherein:
$R_1$ = hydrogen, saturated or unsaturated $C_1$-$C_{10}$ alkyl
$R_2$ = saturated or unsaturated $C_1$-$C_{10}$
$R_3$ = hydrogen or benzoyl having insecticide activity characterized by the operations of:

(a) photoisomerizing by artificial illumination in polar and non polar solvents a trans-enedicarbonylic intermediate of general formula:

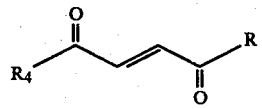
(II)

wherein:

$R = C_4$-$C_{10}$ alkyl and $R_4 = R_2$ to the cis-enedicarbonylic compound with formula:

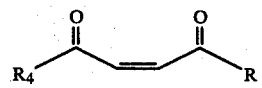
(III)

wherein:
$R = C_4$-$C_{10}$ alkyl, $R_4 = R_2$ (b) cyclizing the cis-enedicarbonylic compound to the corresponding rethrolone of formula (I) by treatment with organic and inorganic bases in solvents constituted of water and a dipolar aprotic solvent at 20°-100° C. temperature.

It is to be noted that the photoisomerization (a) is preferably effected with the compound (II) dissolved in acetone, by mercury vapour lamps irradiation (e.g. by 125 Watt ILESA lamps) for a time from 30 minutes to 1 hour. Afterwards the solvent is evaporated and the chromatography over silica gel is made.

Yields of 80–90% of (III) are obtained while the residue of (II) is recovered. Solvents different from acetone, such as benzene, dioxane or methanol, can be used too. In the cyclization phase (b) the solvent component of the water + solvent mixture is preferably tetrahydropyrane, dioxane or tetrahydrofuran.

The invention will be now described by the following examples with particular reference to its specific working embodiments reported as illustrative and not in a limiting sense.

EXAMPLE 1

26.5 ml of n.BuLi 1.32 N were added to 3 g of 2-methyl-furan dissolved in 20 ml of anhydrous THF, at −25° C., under nitrogen. The mixture was stirred for 4 hours at −15° C., then, again at −25° C. 5 mmoles of R-Br were added, dissolved in 15 ml of anhydrous THF; the mixture was left under stirring for 1.5 hour at −15° C., at room temperature overnight. Then 50 ml of NH4Cl cold saturated solution were added and the mixture was stirred for 1 hour. The organic phase was separated and the aqueous phase was repeatedly extracted by ethyl ether.

The neutral ethereous extracts were dried over Na2SO4.

By solvent evaporation a raw product was obtained which was chromatographed over SiO2. The elution with n-hexane yields the compounds (IV) with 70% yield.

EXAMPLE 2

4 mmoles of PCC were added under stirring to 1 mmole of IV, dissolved in 150 ml of anhydrous $CH_2Cl_2$. The mixture was kept under stirring for 9 hours at 50° C. Then 150 ml of ethyl ether were added and the stirring was continued for another 30 minutes. The organic phase was filtered over $SiO_2$. The residue which was in the reactor was washed several times with ethyl ether as described above, until the residue was reduced to powder. The filtered solutions were collected and the solvent was evaporated.

The so obtained raw product was chromatographed over $SiO_2$. The elution with 2:1 n hexane/ethyl ether yield 3.6 mmoles of II.

EXAMPLE 3

1 g of II, dissolved in 200 ml of acetone Uvasol, after nitrogen was scrubbed in the solution for 30 minutes, was irradiated with an ILESA medium pressure mercury lamp (125 Watt) in an immersion reactor like the one described by R. Svinivasan, Organic Photochemical Synthesis, Vol. I, 1971 Page 1. After a sufficient time the solvent was evaporated and the raw product chromatographed over $SiO_2$ by elution with benzene/ethyl ether 95/5. In this manner the pure compounds of formula (III) were obtained.

EXAMPLE 4

1 g of III was dissolved in 100 ml of fresh distilled dioxane; 100 ml of a 0.1 N NaOH solution at 20° C. under stirring were added to this solution. After 2 hours the mixture was scrubbed in water and extracted several times with ethyl ether. The neutral ethereous extracts were dried over $Na_2SO_4$ and the solvent was evaporated.

The raw product was chromatographed over silica by elution with ethyl acetate. The so obtained product was dissolved in 26 ml of anhydrous pyridine and 4 ml of a 2:1 pyridine and benzoyl chloride were added. 20 ml of water were added after 4 hours.

After 15 minutes the mixture was extracted by ethyl ether several times. The ethereous extracts were washed with 2 N HCl, 2 N NaOH in this order and then with a saturated solution of NaCl up to neutrality. The neutral ethereous extracts were dried over $Na_2SO_4$ and the solvent was evaporated. The raw product obtained was chromatographed over $SiO_2$ by elution with 2:1 n-hexane/ethyl ether. Two 3-keto-cyclopentenes I were obtained having the above indicated $R_1$, $R_2$ and $R_3$.

EXAMPLE 5

1 g of cis-3.8-nonadiene-2.5-dione dissolved in 50 ml of dioxane at 100° C. was added dropwise to 50 ml fresh distilled dioxane solution and to 50 ml 0.1 N NaOH solution. After 1 hour the mixture was mixed in a saturated NaCl solution and extracted several times with ethyl ether. The neutral ethereous extracts were dried over $Na_2SO_4$ and the solvent was evaporated. The raw product was chromatographed over $SiO_2$. The elution with ethyl acetate yield 500 mg of (±) pure allethrone.

The present invention has been described in its preferred embodiment, but it is understood that execution variations can be practically effected by a worker skilled in the art, without departing from the scope thereof.

What is claimed is:

1. A process for the synthesis of the 3-keto-cyclopentene-5-oxy derivatives (rethrolones) with general formula:

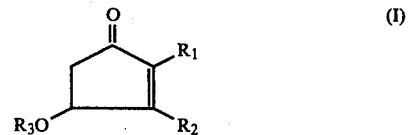

wherein:
$R_1$ = Hydrogen, saturated or unsaturated $C_1$–$C_{10}$ alkyl
$R_2$ = Saturated or unsaturated $C_1$–$C_{10}$ alkyl
$R_3$ = Hydrogen having insecticide activity characterized by the operations of:

(a) Photoisomerizing by artificial illumination in polar and non polar solvents a trans-enedicarbonylic intermediate with general formula:

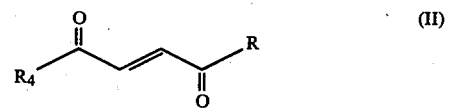

wherein:
R = $C_4$–$C_{10}$ alkyl and
$R_4$ = $R_2$ to the cis-enedicarbonylic compound with formula

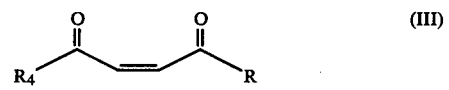

(b) Cyclizing the (III) compound to the corresponding rethrolone of formula (I) by treatment with organic or inorganic bases in solvents constituted of water and an aprotic dipolar solvent at temperature of 20°–100° C.

2. A process according to claim 1, wherein the photoisomerization (a) is effected on (II) compound dissolved in acetone by irradiation with a 125 Watt medium pressure mercury vapor lamp, for 30 minutes up to 1 hour.

3. A process according to any one of claims 1 or 2, wherein as solvent benzene dioxane or methanol is used in the photoisomerization operation (a).

4. A process according to any one of claims 1 or 2, wherein in the cyclization (b) tethrahydrofuran-tethrahydropyrane or dioxane is used as aprotic dipolar solvent.

5. A process according to any one of claim 1 or 2 wherein the photoisomerization operation (a) is effected over a trans-enedicarbonylic compound of formula II:

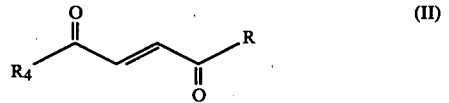

wherein $R_4$ is methyl.

6. A process according to claim 5 wherein the cis-enedicarbonylic compound of formula III:

wherein R$_4$=methyl is treated with 0.1 N NaOH for 2 hours at 20° C., to form the mixture constituted of:

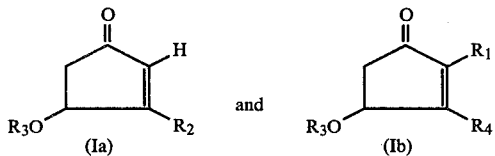

wherein R$_1$, R$_2$ and R$_3$ have the aforesaid meaning for (I) and R$_4$ is methyl.

7. A process according to claim 6 wherein the compounds of formula Ia and Ib react with benzoyl chloride in pyridine to give:

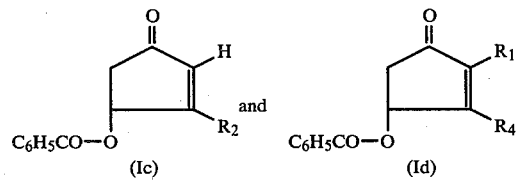

wherein R$_1$ and R$_2$ have the meaning before defined for (I) and R$_4$=methyl.

8. A process according to claim 5 wherein the cis-enedicarbonylic compound of formula (III) with R$_4$=methyl is reacted with 0.1 N NaOH at 100° C. in dioxane to give the 3-keto-cyclopentene-5-oxy derivative with general formula:

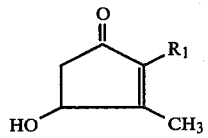

wherein R$_1$ has the meaning before defined for (I).

9. A process according to claims 1 or 2 wherein benzene dioxane or methanol is used as a solvent in the photoisomerization step, and tetrahydrofuran, tetrahydropyrane, or dioxane is used as an aprotic dipolar solvent in the cyclization step.

10. A process according to claims 1 or 2 wherein R$_4$ in the trans-enedicarbonylic compound is methyl, and benzene dioxane or methanol is used as a solvent in the photoisomerization step.

11. A process according to claims 1 or 2 wherein R$_4$ in the trans-enedicarbonylic compound is methyl and tetrahydrofuran, tetrahydropyrane or dioxane is used as an aprotic dipolar solvent in the cyclization step.

12. A process according to claims 1 or 2 wherein R$_4$ in the trans-enedicarbonylic compound is methyl, benzene dioxane or methanol is used as a solvent in the photoisomerization step, and tetrahydrofuran, tetrahydropyrane, or dioxane is used as an aprotic dipolar solvent in the cyclization step.

13. A process according to claim 11, wherein the cisenedicarbonylic compound formed in the photoisomerization step is treated with 0.1 N NaOH for 2 hours at 20° C.

14. A process according to claim 11 wherein the cis-enedicarbonylic compound formed in the photoisomerization step is treated with 0.1 N NaOH for 2 hours at 20° C.

15. A process according to claim 14 wherein the cis-enedicarbonylic compound formed in the isomerization step is treated with 0.1 N NaOH for 2 hours at 20° C.

16. A process wherein the rethrolone formed according to claim 1 is reacted with a benzoyl compound to form a rethrolone wherein the R$_3$ substituent is replaced with benzoyl.

17. A process according to claim 16 wherein the rethrolone is reacted with benzoyl chloride in pyridine.

18. A process according to claim 13 wherein the rethrolone is reacted with benzoyl chloride in pyridine to form a rethrolone wherein the R$_3$ substituent is replaced with benzoyl.

19. A process according to claim 14 wherein the rethrolone is reacted with benzoyl chloride in pyridine to form a rethrolone wherein the R$_3$ substituent is replaced with benzoyl.

20. A process according to claim 15 wherein the rethrolone is reached with benzoyl chloride in pyridine to form a rethrolone wherein the R$_3$ substituent is replaced with benzoyl.

* * * * *